(12) United States Patent
Kawagishi

(10) Patent No.: US 11,200,978 B2
(45) Date of Patent: Dec. 14, 2021

(54) INFORMATION PROCESSING APPARATUS, INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventor: Masami Kawagishi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 101 days.

(21) Appl. No.: 16/834,225

(22) Filed: Mar. 30, 2020

(65) Prior Publication Data

US 2020/0335202 A1 Oct. 22, 2020

(30) Foreign Application Priority Data

Apr. 17, 2019 (JP) .............................. JP2019-078889

(51) Int. Cl.
*G06K 9/00* (2006.01)
*G16H 30/40* (2018.01)
(Continued)

(52) U.S. Cl.
CPC ........... *G16H 30/40* (2018.01); *G06K 9/3233* (2013.01); *G06N 20/00* (2019.01); *G06T 7/0016* (2013.01);
(Continued)

(58) Field of Classification Search
CPC ............. H01L 51/0001; H01L 51/0036; H01L 51/0533; H01L 51/0545; H01L 51/055;
(Continued)

(56) References Cited

U.S. PATENT DOCUMENTS 6,067,373 A * 5/2000 Ishida .................... G06T 3/0068
378/98.12
2002/0090126 A1* 7/2002 Oosawa .................... G06T 7/11
382/132
(Continued)

FOREIGN PATENT DOCUMENTS

JP 2010-200840 A 9/2010

OTHER PUBLICATIONS

Beg, et al., Computing Large Deformation Metric Mappings via Geodesic Flows of Diffeomorphisms, International Journal of Computer Vision, 61(2), Feb. 2005, pp. 139-157.

*Primary Examiner* — Xin Jia
(74) *Attorney, Agent, or Firm* — Canon U.S.A., Inc. IP Division

(57) ABSTRACT

An information processing apparatus includes an obtaining unit, an inference section, and a selection unit. The obtaining unit is configured to obtain a temporal subtraction image between a first medical image captured at a first point of time and a second medical image captured at a second point of time. The inference section includes a plurality of inference units, each for making an inference from the temporal subtraction image. The selection unit is configured to select, based on a region of interest in the obtained temporal subtraction image, at least one inference unit from the plurality of inference units in the inference section. In response to being selected by the selection unit, the at least one inference unit so selected makes the inference from the temporal subtraction image.

18 Claims, 8 Drawing Sheets

(51) Int. Cl.
  *G16H 30/20* (2018.01)
  *G06K 9/32* (2006.01)
  *G06N 20/00* (2019.01)
  *G06T 7/00* (2017.01)

(52) U.S. Cl.
  CPC ... *G16H 30/20* (2018.01); *G06T 2207/10081* (2013.01); *G06T 2207/10116* (2013.01)

(58) Field of Classification Search
  CPC .. G06K 2209/05; G06K 9/3233; G06N 20/00; G06T 2207/10081; G06T 2207/10116; G06T 2207/20084; G06T 2207/30004; G06T 7/0016; G16H 30/20; G16H 30/40
  See application file for complete search history.

(56) References Cited

U.S. PATENT DOCUMENTS

| | | | |
|---|---|---|---|
| 2007/0195932 A1* | 8/2007 | Nakaura | A61B 6/504 378/98.12 |
| 2009/0074276 A1* | 3/2009 | Doi | G06T 5/50 382/130 |
| 2017/0091919 A1* | 3/2017 | Karino | G06K 9/00214 |

* cited by examiner

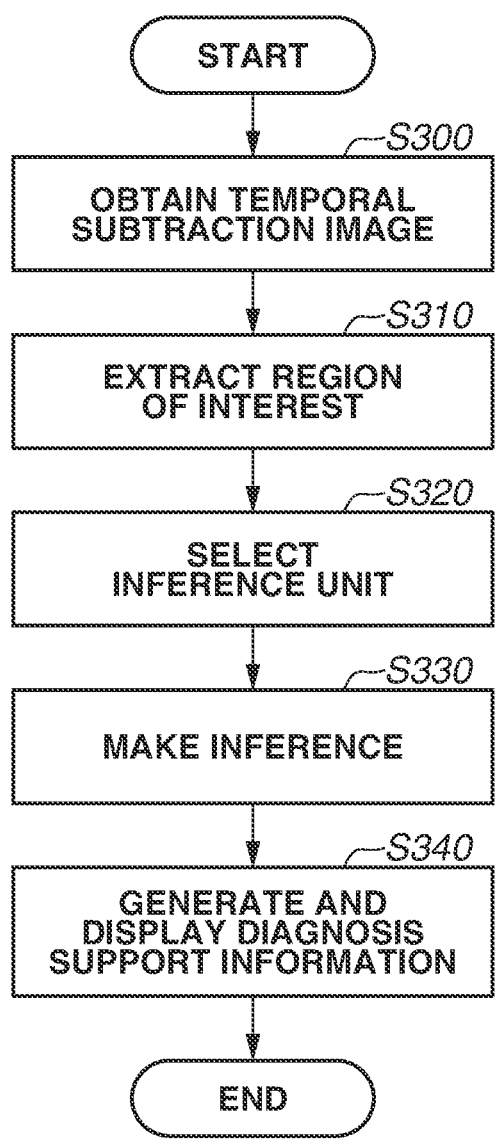

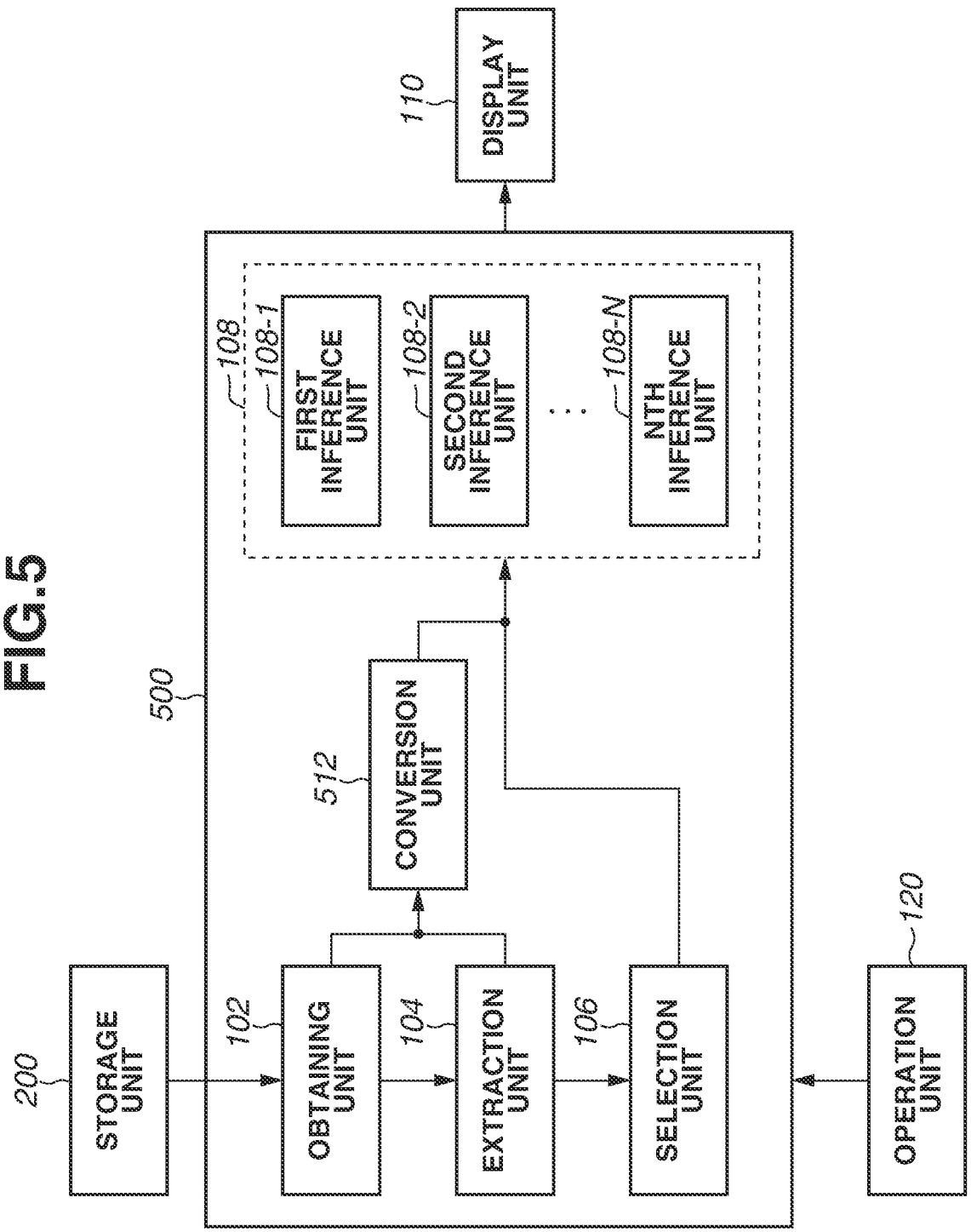

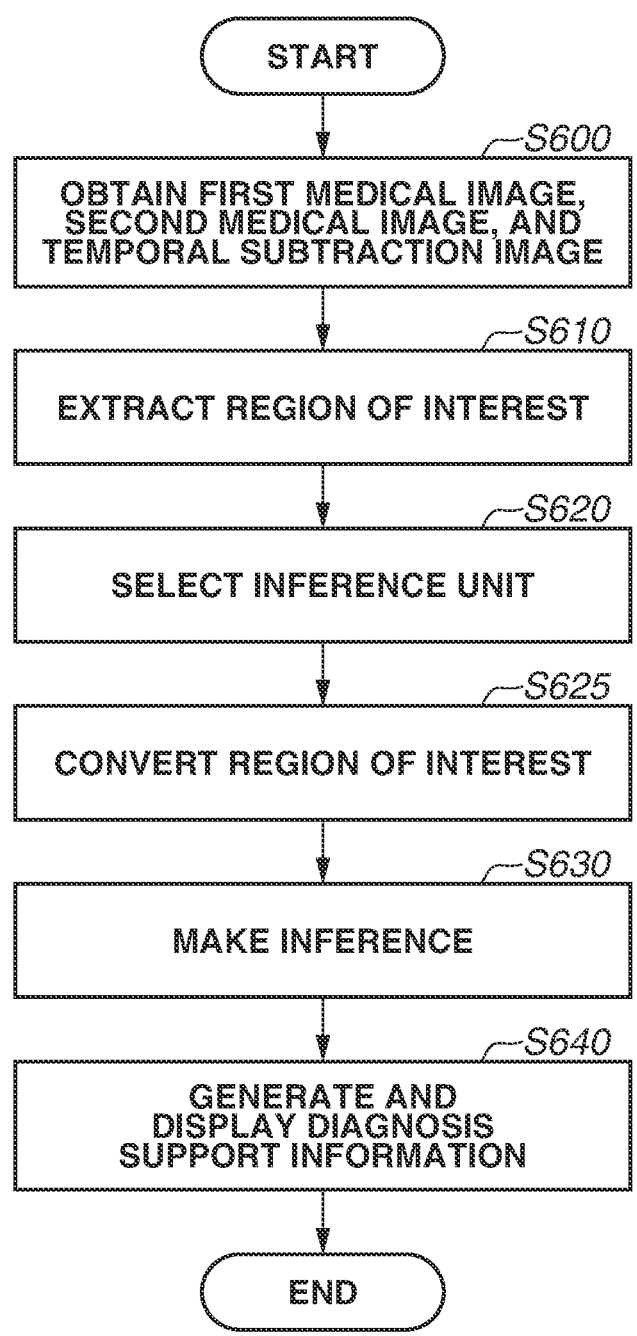

INFORMATION PROCESSING APPARATUS, INFORMATION PROCESSING METHOD, AND NON-TRANSITORY COMPUTER-READABLE STORAGE MEDIUM

BACKGROUND

Field

The present disclosure relates to an information processing apparatus, an information processing method, and a non-transitory computer-readable storage medium for selecting an inference unit that makes an inference from a temporal subtraction image.

Description of the Related Art

There have been techniques for providing diagnostic support for a doctor who is a user by using a machine learning technique (inference unit) on an obtained medical image.

Japanese Patent Application Laid-Open No. 2010-200840 discusses a technique for making a differential diagnosis of an abnormal shadow by using a medical image and image findings pertaining thereto, and displaying the result of the diagnosis as well as information about an image finding or findings that a computer determines to be negative for the result of the diagnosis among the image findings.

SUMMARY

The present disclosure features, among other things, providing a technique for selecting an appropriate inference unit based on a temporal subtraction image between medical images.

In accordance with an aspect of the present disclosure, in a case where there is a plurality of different inference units, an appropriate inference unit may be selected by the user.

In accordance with another aspect of the present disclosure, an information processing apparatus includes an obtaining unit, an inference section, and a selection unit. The obtaining unit is configured to obtain a temporal subtraction image between a first medical image captured at a first point of time and a second medical image captured at a second point of time. The inference section includes a plurality of inference units, each for making an inference from the temporal subtraction image. The selection unit is configured to select, based on a region of interest in the obtained temporal subtraction image, at least one inference unit from the plurality of inference units in the inference section. In response to being selected by the selection unit, the at least one inference unit so selected makes the inference from the temporal subtraction image.

Further features of the present disclosure will become apparent from the following description of exemplary embodiments with reference to the attached drawings.

BRIEF DESCRIPTION OF THE DRAWINGS

FIG. 3 is a flowchart illustrating an example of processing by the information processing apparatus.

FIG. 5 is a diagram illustrating another example of a functional configuration of an information processing apparatus.

FIG. 6 is a flowchart illustrating another example of processing by the information processing apparatus.

DESCRIPTION OF THE EMBODIMENTS

Exemplary embodiments of the present disclosure will be described below with reference to the drawings.

An information processing apparatus according to a first exemplary embodiment extracts a region of interest from a temporal subtraction image between medical images of a subject at two different points of time, and selects an inference unit based on the extracted region of interest. In the following description, the target medical images are chest X-ray computed tomography (CT) images (three-dimensional images). As employed herein, images at two points of time are medical images of the same patient. The target medical images are, however, not limited thereto, and all the target medical images are merely examples for describing processes of the information processing apparatus.

Figure 1:
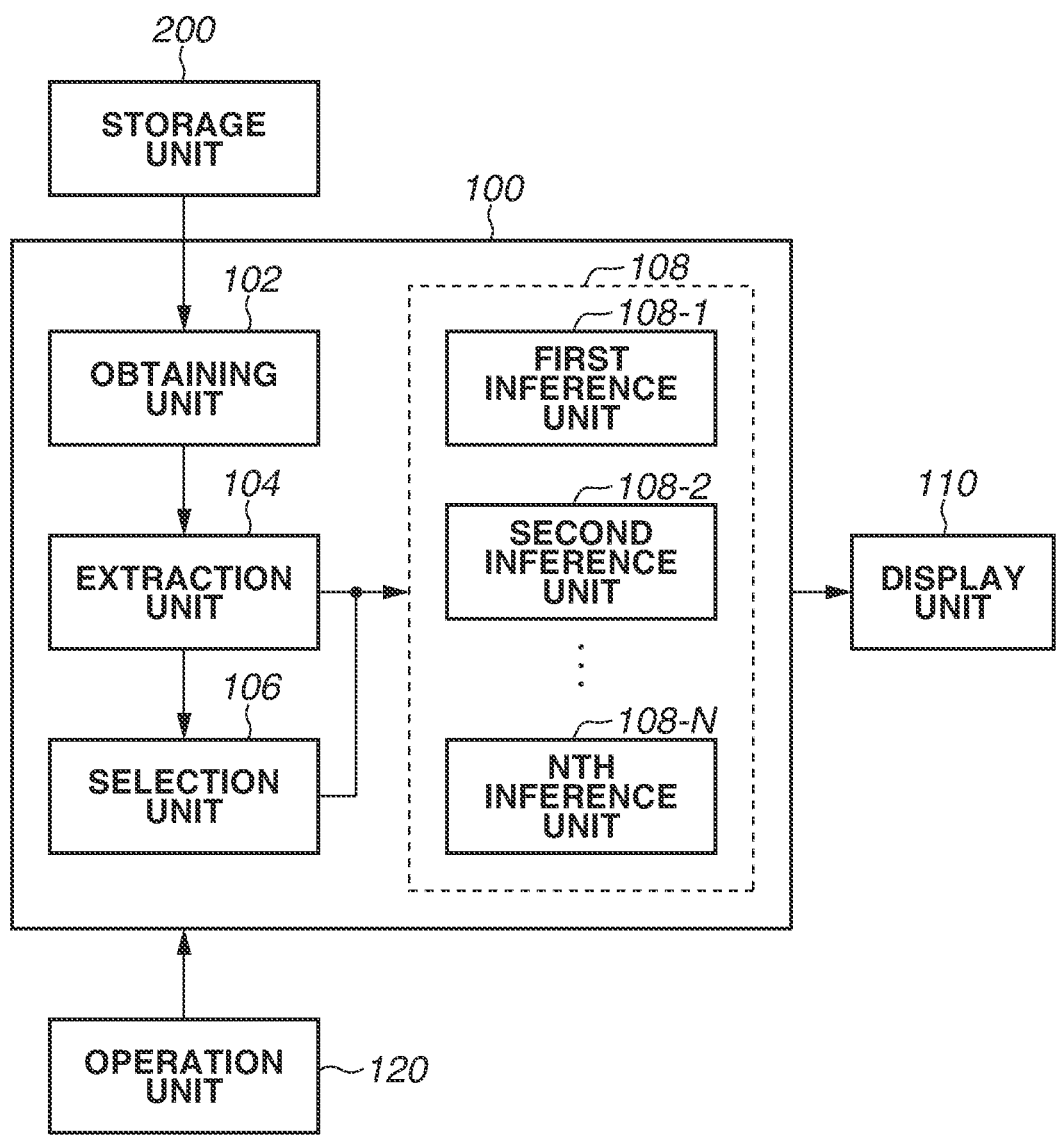
FIG. 1 is a diagram illustrating an example of a functional configuration of an information processing apparatus.

FIG. 1 is a diagram illustrating an example of a functional configuration of an information processing apparatus 100 according to the first exemplary embodiment. The information processing apparatus 100 according to the present exemplary embodiment is connected to a storage unit 200 that stores medical images including temporal subtraction images, and information including clinical information. However, the information stored in the storage unit 200 is not limited thereto, and the date and time of imaging and imaging conditions may be stored instead. The storage unit 200 may be a picture archiving and communication system (PACS), an electronic medical chart, or a radiogram interpretation report, and information including a temporal subtraction image may be obtained based on a request from the information processing apparatus 100. A display unit 110 displays an inference result of the information processing apparatus 100 as diagnosis support information. Additional user inputs may be accepted by an operation unit 120.

The information processing apparatus 100 includes an obtaining unit 102, an extraction unit 104, a selection unit 106, and an inference section 108. The obtaining unit 102 obtains a temporal subtraction image. The extraction unit 104 extracts a region of interest from the temporal subtraction image. The selection unit 106 selects an inference unit from the inference section 108. The inference section 108 includes first to Nth inference units 108-1 to 108-N. The obtaining unit 102 issues a request to the storage unit 200 and obtains a temporal subtraction image between a first medical image captured of a target patient (subject) at a first point of time and a second medical image captured of the target patient at a second point of time. Details of the temporal subtraction image will be described below. The extraction unit 104 extracts a region of interest from the temporal subtraction image. Specifically, the region of interest in the temporal subtraction image is at least part of a region indicating an abnormal shadow on at least either one of the first and second medical images. The selection unit 106 selects at least one inference unit 108-I from the first to Nth inference units 108-1 to 108-N of the inference section 108 based on the region of interest. The selection unit 106 selects input information to be input to the selected inference unit 108-I. The selected inference unit 108-I makes an inference about the subject based on information including the region of interest. The first to Nth inference units 108-1 to 108-N make respectively different inferences. Details will be described below. The display unit 110 displays the result of the inference made by the inference unit 108-I as diagnosis support information.

At least some of the units of the information processing apparatus 100 illustrated in FIG. 1 may be implemented as independent devices. The functions of the respective units may be implemented as software. In the present exemplary embodiment, the units are implemented by respective pieces of software.

Figure 2:
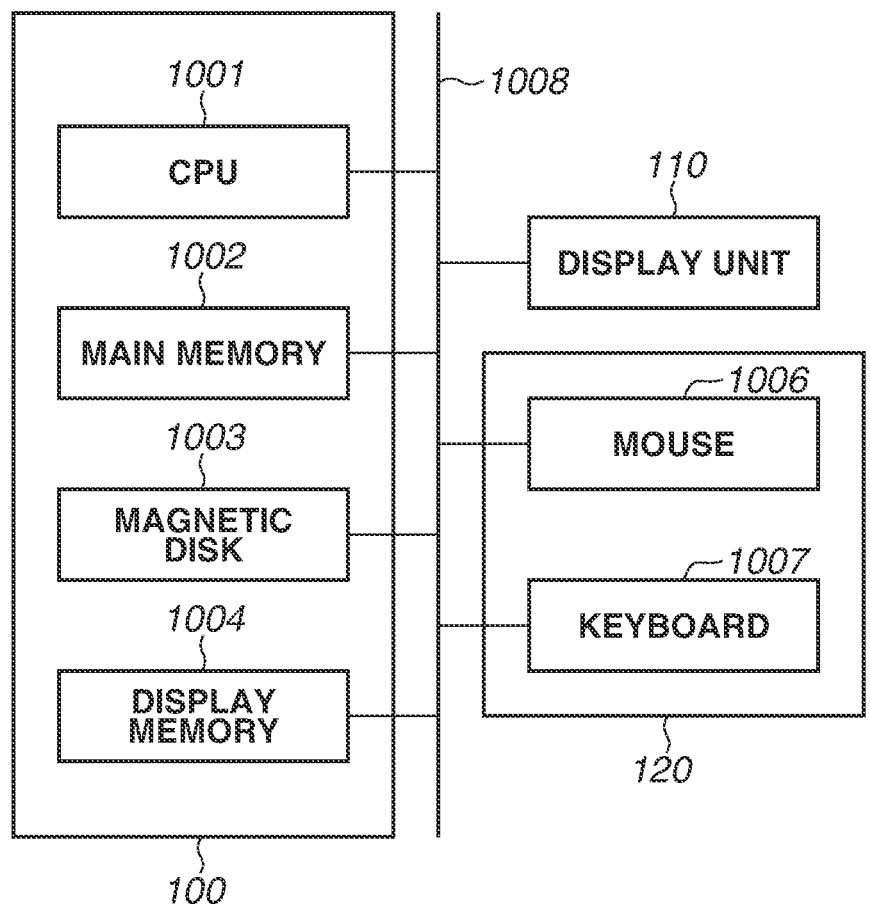
FIG. 2 is a diagram illustrating an example of a hardware configuration of the information processing apparatus.

FIG. 2 is a diagram illustrating an example of a hardware configuration of the information processing apparatus 100. FIG. 2 illustrates the information processing apparatus 100, the display unit 110 such as a monitor, and the operation unit 120 including a mouse 1006 and a keyboard 1007. A central processing unit (CPU) 1001 of the information processing apparatus 100 mainly controls operation of the components. A main memory 1002 stores a control program to be executed by the CPU 1001, and provides a work area during execution of a program by the CPU 1001. A magnetic disk 1003 stores an operating system (OS), device drivers of peripheral devices, and programs for implementing various types of application software including a program for performing processing to be described below. The functions (software) of the information processing apparatus 100 illustrated in FIG. 1 and processing of a flowchart to be described below are implemented by the CPU 1001 executing the programs stored in the main memory 1002 and the magnetic disk 1003. A display memory 1004 temporarily stores display data.

Examples of the display unit 110 include a cathode-ray tube (CRT) monitor and a liquid crystal monitor. The display unit 110 displays images and text based on data from the display memory 1004. The mouse 1006 and the keyboard 1007 in the operation unit 120 accept a pointing input and a text input performed by the user, respectively. The foregoing components are communicably connected to each other by a common bus 1008.

Next, entire processing performed by the information processing apparatus 100 will be described with reference to the flowchart of FIG. 3. FIG. 3 is a flowchart illustrating an example of the processing performed by the information processing apparatus 100. In the present exemplary embodiment, the processing illustrated in FIG. 3 is implemented by the CPU 1001 executing the program for implementing the functions of the respective units, stored in the main memory 1002.

In step S300, the obtaining unit 102 issues a request to the storage unit 200 and obtains a temporal subtraction image between a first medical image captured of a target patient at a first point of time and a second medical image captured of the target patient at a second point of time. At this time, the second point of time is closer to the current point of time (in other words, the first medical image is captured before the second medical image). The temporal subtraction image is generated by subtracting the first medical image registered to the second medical image from the second medical image. The registration is performed by using a conventional rigid registration technique or non-rigid registration technique (for example, M F. Beg et al., "Computing Large Deformation Metric Mappings via Geodesic Flows of Diffeomorphisms", International Journal of Computer Vision, 61(2), 139-157, 2005).

In step S310, the extraction unit 104 extracts a region of interest from the temporal subtraction image obtained in step S300. The region of interest may be extracted based on a parameter set for the temporal subtraction image in advance. A region selected by the user via a graphical user interface (GUI) using the operation unit 120 may be extracted as the region of interest.

Figure 4C:
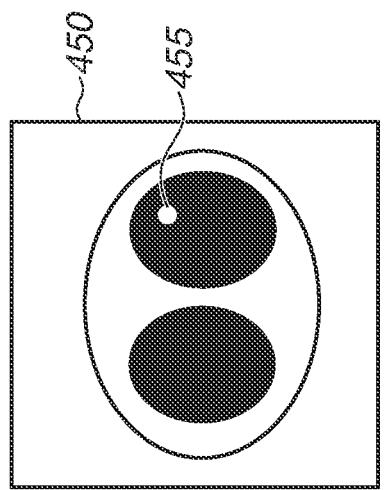
FIGS. 4A, 4B, and 4C are diagrams illustrating an example of a temporal subtraction image.
Figure 4B:
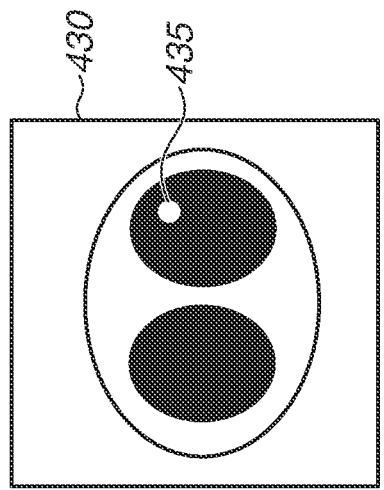
Figure 4A:
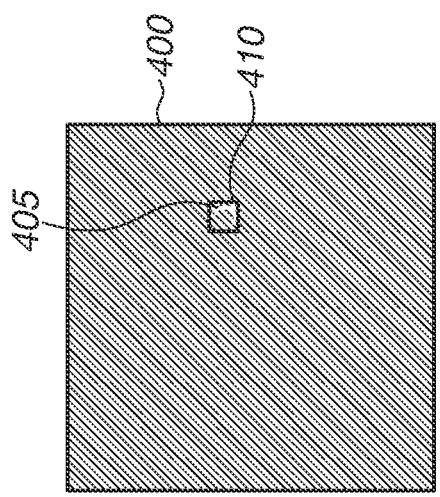

A simple example of the temporal subtraction image will be described with reference to FIGS. 4A, 4B, and 4C. FIG. 4B illustrates a first medical image 430. FIG. 4C illustrates a second medical image 450. A first nodule region 435 is drawn in the first medical image 430, and a second nodule region 455 in the second medical image 450. Subtracting the first medical image 430 from the second medical image 450 produces a temporal subtraction image 400 illustrated in FIG. 4A. FIG. 4A illustrates a slice (two-dimensional image) of the temporal subtraction image 400. The temporal subtraction image 400 according to the present exemplary embodiment expresses the result of the subtraction in such a manner that areas having a value of 0 are in gray, areas having a positive value in white, and areas having a negative value in black. In other words, white areas represent where the second medical image has an increased value compared to the first medical image. Black areas represent where the second medical image has a decreased value compared to the first medical image. Specifically, if a lesion is found in an area where values have changed as a result of the subtraction and the values are positive (white area on the temporal subtraction image), it indicates that the lesion has increased in size. On the other hand, if, as a result of the subtraction, the values are negative (black area on the temporal subtraction image), it indicates that the lesion has decreased in size. If there is a lesion in an area of the temporal subtraction image 400 where the values (white area) have increased, the selection unit 106 selects an inference unit that makes a differential diagnosis, or an inference unit that makes a prognosis for evaluating a prognostic implication of the lesion. If the shape of a white area is that of a lesion, the selection unit 106 selects an inference unit that makes a cancer risk evaluation. Depending on the type of captured images, the imaged part, and the target of diagnosis, the relationship between the increase and decrease in the size of a lesion and the increase and decrease in value may be different.

In the example of FIGS. 4A to 4C, a feature region 405 on the temporal subtraction image 400 is displayed as a white area. This indicates that the lesion size has increased at the point of time when the second medical image 450 is captured, compared to the point of time when the first medical image 430 is captured. In the example of FIGS. 4A to 4C, the extraction unit 104 extracts a cube (in FIG. 4A, illustrated as a square) surrounding the feature region 405 (white area) as a region of interest 410.

In step S320, the selection unit 106 selects an inference unit 108-I from the first to Nth inference units 108-1 to 108-N based on the region of interest 410 extracted in step S310. In the following description, the inference section 108 is described to include an inference unit that makes a differential diagnosis of a nodular shadow, an inference unit that makes a prognosis, an inference unit that makes a therapy evaluation, and an inference unit that makes a risk assessment of lung cancer. The inference units constituting the inference section 108, however, are not limited thereto, and other inference units may be included. Any type of conventional machine learning unit may be used as an inference unit. Examples include a convolutional neural network (CNN), a support vector machine (SVM), and a Bayesian network. Depending on the target of inference, different machine learning units may be used as the machine learning units. A plurality of machine learning units may be combined. In the present exemplary embodiment, CNNs are used as the machine learning units of the respective inference units.

Here, the selection unit 106 selects the inference unit 108-I based on the shape and volume of the feature region 405 that constitutes a feature amount included in the region of interest 410 on the temporal subtraction image 400. In the temporal subtraction image 400, the shape of the feature region 405 in the region of interest 410 does not match a spherical shape that can be found in a nodular shadow or a hazy or cloudy appearance that can be found in a diffuse lung disease, and the volume of the feature region 405 is smaller than that of a normal nodular shadow. As employed herein, a hazy or cloudy appearance refers to a wide region drawn in light color (cloudy white area), including a mixture of a region that has CT values greater than that of the surrounding lung field (air region) and appears white and the air region. However, such a definition is an example, and different determination methods using a texture suggesting a diffuse lung disease may be used. The selection unit 106 thus selects an inference unit that evaluates a prognostic implication as the inference unit 108-I from the inference section 108 based on a feature amount including information about the feature region 405 in the region of interest 410. By contrast, if the volume of the feature region 405 constituting the feature amount in the region of interest 410 does not have much difference from that of a nodular shadow, the selection unit 106 selects an inference unit that makes a differential diagnosis as the inference unit 108-I. The selection unit 106 changes the inference unit to be selected depending on the feature amount in the region of interest 410. Specifically, the selection unit 106 is characterized by selecting a first inference unit from the plurality of inference units if the region of interest 410 has a first feature amount, and selecting a second inference unit different from the first inference unit if the region of interest 410 has a second feature amount. The selection unit 106 selects an inference unit based on at least one of the shape, size, and pixel values (whether the pixel values resulting from the subtraction are positive or negative) of the feature region 405 constituting the feature amount in the region of interest 410. In step S330, the inference unit 108-I selected by the selection unit 106 in step S320 makes an inference based on the region of interest 410 extracted in step S310. Input information for the inference unit 108-I is at least either the temporal subtraction image 400 or the region of interest 410 on the temporal subtraction image 400. As described above, the inference is made by using a three-dimensional CNN (3D-CNN) with the region of interest 410 (cube) as an input.

In step S340, the display unit 110 generates diagnosis support information based on the result of the inference made by the inference unit 108-I in step S330, and displays the diagnosis support information to the user. Such a prognostic implication can imply a future change of the lesion area and assist generation of a corresponding medical procedure plan.

In the present exemplary embodiment, the obtaining unit 102 obtains the temporal subtraction image 400 between the first medical image 430 captured of the target patient at the first point of time and the second medical image 450 captured of the target patient at the second point of time. The selection unit 106 selects an inference unit 108-I from the plurality of inference units 108-1 to 108-N based on the region of interest 410 extracted by the extraction unit 104 in the temporal subtraction image 400. The selected inference unit 108-I makes an inference about the target patient. The display unit 110 generates diagnosis support information from the result of the inference, and displays the diagnosis support information to the user. Since the selection unit 106 selects an appropriate inference unit from the plurality of inference units 108-1 to 108-N based on the region of interest 410 in the temporal subtraction image 400, appropriate diagnosis support information can be generated and displayed. In other words, the information processing apparatus 100 according to the present exemplary embodiment is characterized by including the obtaining unit 102 that obtains a temporal subtraction image between a first medical image captured at a first point of time and a second medical image captured at a second point of time, the inference section 108 including the plurality of inference units 108-1 to 108-N that make an inference from the temporal subtraction image, and the selection unit 106 that selects at least one inference unit from the plurality of inference units 108-1 to 108-N in the inference section 108 based on a region of interest in the obtained temporal subtraction image.

An information processing apparatus 500 according to a second exemplary embodiment illustrated in FIG. 5 differs from the information processing apparatus 100 according to the first exemplary embodiment in the following aspects. An obtaining unit 102 obtains a first medical image and/or a second medical image as well as a temporal subtraction image. A conversion unit 512 converts a region of interest on the temporal subtraction image so that the region of interest is substantially consistent with the second medical image, and uses the region of interest on the second medical image as an input to an inference unit 108-I. FIG. 5 is a diagram illustrating an example of a functional configuration of the information processing apparatus 500 according to the second exemplary embodiment. As for components denoted by the same reference numerals as in FIG. 1, only differences from the first exemplary embodiment will be described.

The obtaining unit 102 issues a request to a storage unit 200 and obtains a first medical image captured of a target patient at a first point of time, a second medical image captured of the target patient at a second point of time, and a temporal subtraction image between the first and second medical images. The conversion unit 512 makes a region of interest in the temporal subtraction image correspond to the first medical image and/or the second medical image based on an inference unit 108-I selected by a selection unit 106. Specifically, the conversion unit 512 performs conversion to make the region of interest correspond to the second medical image. The selected inference unit 108-I makes an inference about the target patient based on information within the region made substantially consistent. In other words, the information input to the inference unit 108-I is information including a region converted by the conversion unit 512. The information processing apparatus 500 according to the present exemplary embodiment has a like hardware configuration as that of the first exemplary embodiment illustrated in FIG. 2.

Next, entire processing performed by the information processing apparatus 500 will be described with reference to the flowchart of FIG. 6.

In step S600, the obtaining unit 102 issues a request to the storage unit 200 and obtains a first medical image captured of the target patient at a first point of time, a second medical image captured of the target patient at a second point of time, and a temporal subtraction image between the first and second medical images.

Figure 7A:
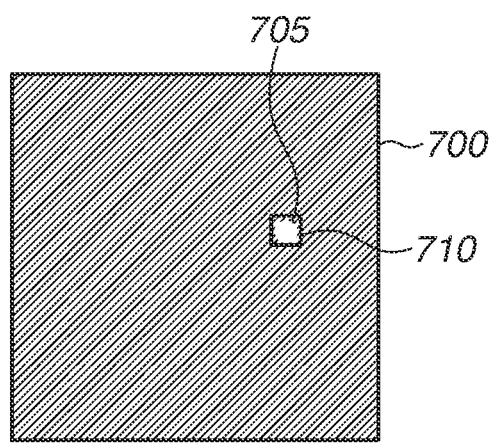
FIGS. 7A and 7B are diagrams illustrating examples of a temporal subtraction image and a second medical image.

The processing of step S610 is like that of step S310 according to the first exemplary embodiment. In the present exemplary embodiment, a region of interest 710 is extracted from a temporal subtraction image 700 illustrated in FIG. 7A.

The processing of step S620 is like that of step S320 according to the first exemplary embodiment. Here, the shape of a white area that is a feature region 705 in the region of interest 710 is that of a nodular shadow. The selection unit 106 thus determines that a shadow not present at the first point of time appears at the second point of time. The selection unit 106 thus selects an inference unit that makes a differential diagnosis for nodules as the inference unit 108-I from among first to Nth inference units 108-1 to 108-N based on a feature amount in the region of interest 710.

Figure 7B:
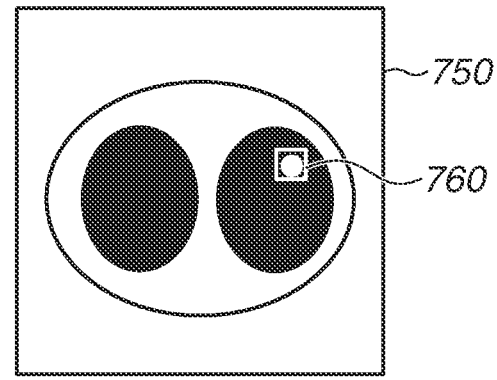

In step S625, the conversion unit 512 converts the region of interest 710 on the temporal subtraction image 700 based on the inference unit 108-I selected in step S620 so that the region of interest 710 is substantially consistent with the first medical image and/or the second medical image obtained in step S600. Specifically, the conversion unit 512 converts XYZ coordinates and a width, height, and depth of the region of interest 710 on the temporal subtraction image 700 so that the region of interest 710 is substantially consistent with the first medical image and/or the second medical image, and assumes the resulting region as a region of interest. For example, converting the region of interest 710 illustrated in FIG. 7A to be substantially consistent with a second medical image 750 illustrated in FIG. 7B produces a region of interest 760 on the second medical image 750.

In the present exemplary embodiment, the shadow is determined to appear at the second point of time, and the inference unit that makes a differential diagnosis for nodules is selected in step S620. The region of interest 710 is therefore converted to be substantially consistent with the second medical image 750 alone, and the converted region is extracted from the second medical image 750. Since information not drawn on the temporal subtraction image 700 can also be used for inference, a more appropriate inference can be made. In the present flowchart, step S620 for selecting an inference unit includes selecting the inference unit 108-I from the inference section 108 based on the information about the region of interest 710 in the temporal subtraction image 700. The region converted in step S625 is then used as the input to the inference unit 108-I. The selection unit 106 may select the inference unit 108-I by taking into account information about the region converted by the conversion unit 512. Such a configuration enables selection of appropriate input information and an appropriate inference unit.

In step S630, the inference unit 108-I selected by the selection unit 106 in step S620 makes an inference based on the region of interest 760 converted to be substantially consistent with the second medical image 750 by the conversion unit 512 in step S625.

The processing of step S640 is like that of step S340 according to the first exemplary embodiment.

In the present exemplary embodiment, the selection unit 106 selects the inference unit 108-I based on the region of interest 710 in the temporal subtraction image 700. The conversion unit 512 converts the region of interest 710 in the temporal subtraction image 700 to be substantially consistent with the second medical image 750. The converted region is used as the input to the inference unit 108-I. Input information appropriate for the inference unit 108-I can accordingly be selected, and more appropriate diagnosis support information can be displayed.

A modification of the second exemplary embodiment will be described. In the second exemplary embodiment, the selection unit 106 determines, in step S620, that the region of interest 710 is a nodular shadow and selects the inference unit 108-I that makes a differential diagnosis for nodules from the inference section 108. However, this is not restrictive. For example, if a cloudy white area appears in the temporal subtraction image, the selection unit 106 may assume this feature region as a region of interest and select an inference unit that makes a risk assessment of lung cancer as the inference unit 108-I. The obtaining unit 102 may obtain second clinical information at the second point of time, and the second clinical information may also be used as an input to the inference section 108.

A third exemplary embodiment will be described. An information processing apparatus according to the third exemplary embodiment differs from the information processing apparatus 100 according to the first exemplary embodiment and the information processing apparatus 500 according to the second exemplary embodiment in the following aspects. An obtaining unit 102 obtains first clinical information at a first point of time and second clinical information at a second point of time in addition to a first medical image and a second medical image. A region of interest on a temporal subtraction image is then converted to be substantially consistent with the first and second medical images. The regions substantially consistent and the first and second clinical information are used as inputs to an inference section 108. For example, the clinical information includes the capturing date of the first medical image, the capturing date of the second medical image, sex, age, a case history, a past medical history, a medicine prescription history, and blood test data before and after the capturing of the first medical image and/or before and after the capturing of the second medical image. Input information to an inference unit includes at least either one of the first and second medical images. The information processing apparatus according to the third exemplary embodiment further includes a conversion unit that makes an obtained region of interest correspond to at least either one of the first and second medical images.

An information processing apparatus 500 according to the third exemplary embodiment has a like functional configuration as that of the information processing apparatus 500 illustrated in FIG. 5. Only differences from the second exemplary embodiment will be described below. The obtaining unit 102 issues a request to a storage unit 200 and obtains a first medical image captured of a target patient at a first point of time, first clinical information, a second medical image captured of the target patient at a second point of time, second clinical information, and a temporal subtraction image between the first and second medical images.

Entire processing performed by the information processing apparatus 500 is like that of the flowchart of FIG. 6, but part of the processing is different. The entire processing performed by the information processing apparatus 500 will be described below with reference to the flowchart of FIG. 6.

In step S600, the obtaining unit 102 issues a request to the storage unit 200 and obtains a first medical image captured of a target patient at a first point of time, first clinical information, a second medical image captured of the target patient at a second point of time, second clinical information, and a temporal subtraction image between the first and second medical images. In other words, the input information includes at least either the clinical information at the first point of time or the clinical information at the second point of time.

Figure 8A:
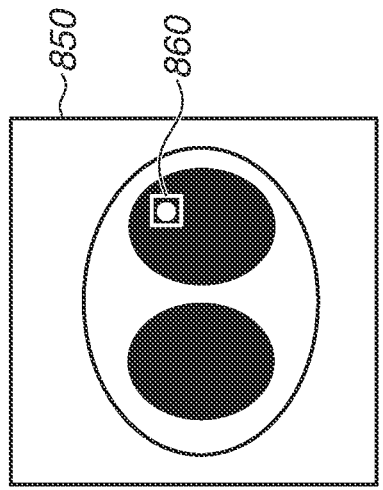
FIGS. 8A, 8B, and 8C are diagrams illustrating examples of a temporal subtraction image, a first medical image, a second medical image, first clinical information, and second clinical information.

The processing of step S610 is like that of step S610 according to the second exemplary embodiment. In the present exemplary embodiment, a region of interest 810 is extracted from a temporal subtraction image 800 illustrated in FIG. 8A.

The processing of step S620 is like that of step S620 according to the second exemplary embodiment. The shape of a black area in a feature region 805 in the region of interest 810 is neither a spherical shape of a nodular shadow nor one with a hazy or cloudy appearance of a diffuse lung disease. In addition, the volume of the black area is smaller than that of a normal nodular shadow. The selection unit 106 therefore selects an inference unit that makes a therapy evaluation as the inference unit 108-I from the inference section 108 including first to Nth reference units 108-1 to 108-N. The selection unit 106 may select the inference unit 108-I by taking into account the clinical information at the first point of time and the clinical information at the second point of time. In other words, the selection unit 106 selects the inference unit 108-I based on at least either the clinical information at the first point of time or the clinical information at the second point of time.

Figure 8B:
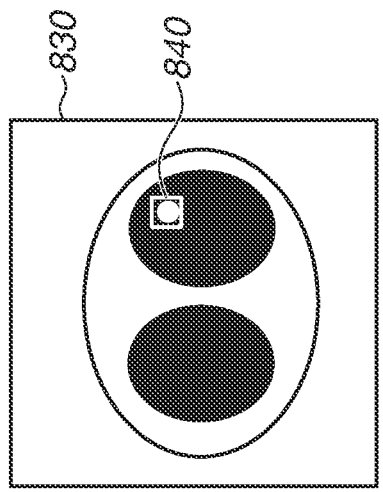
Figure 8C:
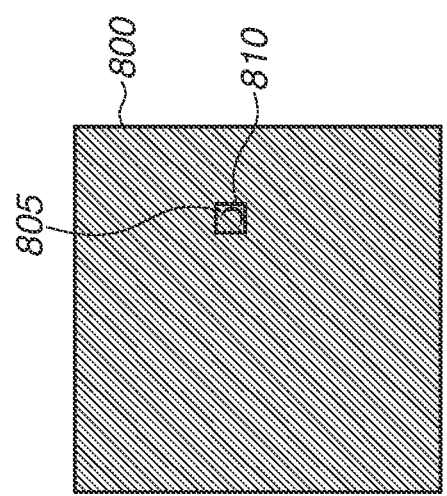

The processing of step S625 is like that of step S625 according to the second exemplary embodiment. In the present exemplary embodiment, the selection unit 106 determines, in step S620, that the shadow has decreased at the second point of time compared to the first point of time, and selects the inference unit that makes a therapy evaluation. The region of interest 810 is thus converted to be substantially consistent with both the first medical image (830 in FIG. 8B) and the second medical image (850 in FIG. 8C). As a result of the conversion, a region of interest 840 (FIG. 8B) substantially consistent with the first medical image 830 and a region of interest 860 (FIG. 8C) substantially consistent with the second medical image 850 are obtained.

In step S630, the inference unit 108-I selected in step S620 makes an inference by using information for inference. Specifically, the inference unit 108-I uses first clinical information 845 (FIG. 8B) at the first point of time and second clinical information 865 (FIG. 8C) at the second point of time that are obtained in step S600. The region of interest 840 converted to be substantially consistent with the first medical image 830 and the region of interest 860 converted to be substantially consistent with the second medical image 850, that are obtained in step S625 are also used. Handling the clinical information as if it were images allows application of the inference unit 108-I that is a CNN. The inference section 108 may include machine learning units that use values themselves like SVMs and Bayesian networks.

The processing of step S640 is like that of step S640 according to the second exemplary embodiment.

In the present exemplary embodiment, the region of interest 810 on the temporal subtraction image 800 is converted to be substantially consistent with the first and second medical images 830 and 850, and the converted regions 840 and 860 are used as inputs to the inference section 108. More appropriate diagnosis support information can be displayed by also using the first clinical information at the first point of time and the second clinical information at the second point of time for inference.

A first modification will be described. In the first to third exemplary embodiments, the number of regions of interest is described to be one. However, there may be a plurality of regions of interest. Different inference units may be selected for the plurality of respective regions of interest. According to such a method, comprehensive support information about the target images can be displayed since an appropriate inference unit can be selected for each individual region of interest.

In a case where there is a plurality of feature regions, the selection unit 106 may perform processing for associating the feature regions with respective regions of interest. The selection unit 106 may select different inference units for the respective associated regions of interest.

A second modification will be described. In the first to third exemplary embodiments, one inference unit is selected for each region of interest. However, a plurality of inference units may be selected for each region of interest. According to such a configuration, various types of support information can be displayed for a region of interest. This allows the user to make a diagnosis by taking into account the inference results for the respective regions of interest by the plurality of inference units and select appropriate support information for the target images from among pieces of support information that are displayed.

A third modification will be described. In the first to third exemplary embodiments, the obtaining unit 102 obtains respectively different sets of information. However, the obtaining unit 102 may obtain all the information, and information to be used may be selected from the obtained information based on the inference unit 108-I selected by the selection unit 106. Alternatively, the obtaining unit 102 may initially obtain a temporal subtraction image alone, and information to be used may be requested from the storage unit 200 based on the inference unit 108-I each time.

A fourth exemplary embodiment will be described. In the first to third exemplary embodiments, either the region of interest in the temporal subtraction image or the region(s) of interest made substantially consistent with the first and/or second medical image(s) is/are input to the inference section 108. However, all the regions of interest may be input to the inference section 108 at a time. The inputs are not limited to the regions of interest, and the entire images or part of the images may be input.

A fifth modification will be described. In the first to third exemplary embodiments, the selection unit 106 selects an inference unit 108-I based on the feature region on the obtained temporal subtraction image, and the selected inference unit 108-I makes an inference about the region of interest. However, for example, the feature region on the temporal subtraction image can lack sufficient information for the selection unit 106 to select an inference unit. Examples of such a case include where the feature region is extremely small and where the feature region exists in a locally scattered manner.

In such cases, unlike the foregoing first to third exemplary embodiments, the region of interest is difficult to identify from the feature region. If the feature region on the temporal subtraction image is insufficient to set a region of interest, the selection unit 106 changes the region of interest. In other words, if the feature region in the region of interest does not satisfy information for selecting an inference unit, the selection unit 106 changes the region of interest. For example, the selection unit 106 may increase the range of the region of interest including the feature region. For the sake of determination, the selection unit 106 may set a lower limit in the size of the region of interest. If the feature region is located in a region smaller than a predetermined size or locally scattered, the selection unit 106 increases the range of the region of interest. According to the configuration of setting a region of interest having a wider range, the amount of information about the region of interest increases when the region of interest is made correspond to the second medical image by the conversion unit 512, compared to a case in which the region where the feature region is located is smaller than the predetermined size. If feature regions are locally scattered, the scattered feature regions are likely to be related to each other. The amount of information increases if the scattered feature regions can be surrounded by a single region of interest. By such a modification, for example, a region of interest including a plurality of feature regions locally scattered can be set, and the accuracy of selection of the inference unit 108-I by the selection unit 106 is thus expected to improve in the first exemplary embodiment. In the second and third exemplary embodiment, the region of interest is converted to be consistent with a medical image or images. In addition to the effects of the first exemplary embodiment, the information about the feature regions and the peripheral areas can thus be further given to the inference unit 108-I, and the accuracy of inference is expected to improve.

A sixth modification will be described. In the foregoing fifth modification, processing in a case where the feature region is extremely small or exists in a locally scattered manner has been described. In the sixth modification, the obtaining unit 102 obtains clinical information if the feature region in the temporal subtraction image does not include sufficient region information to set a region of interest, i.e., if the feature region is extremely small or exists in a locally scattered manner.

For example, the clinical information obtained by the obtaining unit 102 includes the capturing date of the first medical image, the capturing date of the second medical image, sex, age, a case history, a past history, a medicine prescription history, and blood test data before and after the capturing of the first medical image and/or before and after the capturing of the second medical image. If the selection unit 106 has difficulty in setting a region of interest, the selection unit 106 refers to the clinical information and identifies the reason for the difficulty in setting a region of interest for the feature region. For example, a case where there are a sufficient number of days between the capturing date of the first medical image and that of the second medical image and there is a medical prescription history will be described. If a feature region is not sufficiently discernible in the temporal subtraction image despite the sufficient number of days of the imaging interval and the drug prescription history, the selection unit 106 displays via the display unit 110 that no therapeutic effect is observed despite the medication. If there are not a sufficient number of days between the capturing date of the first medical image and the capturing date of the second medical image, the selection unit 106 displays that the number of days between the captured images is not sufficient. In other words, the selection unit 106 identifies the reason why the feature region in the region of interest does not satisfy information for selecting an inference unit based on the clinical information at the first point of time and the clinical information at the second point of time. The selection unit 106 displays the identified reason via the display unit 110.

If the number of days between the captured images is not sufficient, the following processing may be performed. The obtaining unit 102 obtains a temporal subtraction image between a medical image older than the capturing date of the first medical image and the second medical image, if such exists.

Alternatively, the obtaining unit 102 obtains a temporal subtraction image between a medical image newer than the capturing date of the second medical image and the first medical image, if such exists. The obtaining unit 102 may obtain a temporal subtraction image between a different first medical image and a different second medical image, if such exists. In other words, the sixth modification is characterized in that if the feature region in the region of interest does not satisfy information for selecting an inference unit, a temporal subtraction image of which at least either a medical image captured at or before a first point of time or a medical image captured at or after a second point of time is different is obtained, and the temporal subtraction image is obtained and processed. The obtaining unit 102 may obtain a temporal subtraction image generated by replacing a medical image or images, and the selection unit 106 may set a region of interest from the new temporal subtraction image and select an inference unit 108-I. Such processing is not limited to the case where the number of days between the medical images is insufficient. For example, if both the first and second medical images include a similar nodular shadow, the nodular shadow is not displayed on the temporal subtraction image. The present configuration is effective in such a case.

An exemplary embodiment of the present disclosure can also be implemented by processing for supplying a program for implementing one or more functions of the foregoing exemplary embodiments to a system or an apparatus via a network or a storage medium, and reading and executing the program by one or more processors in a computer of the system or apparatus. A circuit for implementing the one or more functions (such as an application specific integrated circuit (ASIC)) can be used for implementation.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the scope of the present disclosure is not limited to the particular disclosed exemplary embodiments. The scope of the following claims is to be accorded the broadest interpretation so as to encompass all such modifications and equivalent structures and functions.

This application claims the benefit of Japanese Patent Application No. 2019-078889, filed Apr. 17, 2019, which is hereby incorporated by reference herein in its entirety.

What is claimed is:

1. An information processing apparatus comprising:
    an obtaining unit configured to obtain a temporal subtraction image between a first medical image captured at a first point of time and a second medical image captured at a second point of time;
    an inference section including a plurality of inference units, each inference unit for making an inference from the temporal subtraction image; and
    a selection unit configured to select, based on a region of interest in the obtained temporal subtraction image, at least one inference unit from the plurality of inference units in the inference section,
    wherein in response to being selected by the selection unit, the at least one inference unit selected by the selected unit makes the inference from the temporal subtraction image.

2. The information processing apparatus according to claim 1, wherein the region of interest is at least part of a region indicating an abnormal shadow on at least either one of the first and second medical images.

3. The information processing apparatus according to claim 1, further comprising a conversion unit configured to make the region of interest in the obtained temporal subtraction image correspond to at least either one of the first and second medical images.

4. The information processing apparatus according to claim 1, wherein the selection unit is configured to further select input information to be input to the selected inference unit.

5. The information processing apparatus according to claim 4, wherein the input information is at least either the temporal subtraction image or the region of interest on the temporal subtraction image.

6. The information processing apparatus according to claim 4, wherein the input information is information including at least either one of the first and second medical images.

7. The information processing apparatus according to claim 4, wherein the input information is information including a region converted by a conversion unit.

8. The information processing apparatus according to claim 4, wherein the input information includes at least either clinical information at the first point of time or clinical information at the second point of time.

9. The information processing apparatus according to claim 1, wherein the selection unit is configured to, if the region of interest includes a first feature amount, select a first inference unit from the plurality of inference units, and if the region of interest includes a second feature amount, select a second inference unit different from the first inference unit from the plurality of inference units.

10. The information processing apparatus according to claim 1, wherein the selection unit is configured to select the inference unit based on at least one of a shape of a feature region in the region of interest on the temporal subtraction image, a size of the feature region, and a pixel value of the feature region.

11. The information processing apparatus according to claim 1, wherein the selection unit is configured to select the inference unit based on at least either clinical information at the first point of time or clinical information at the second point of time.

12. The information processing apparatus according to claim 1, wherein the selection unit is configured to, if a feature region in the region of interest does not satisfy information for selecting an inference unit, change the region of interest.

13. The information processing apparatus according to claim 12, wherein the selection unit is configured to, if the feature region is located in a region smaller than a predetermined size or locally scattered, increase a range of the region of interest.

14. The information processing apparatus according to claim 12, wherein the selection unit is configured to identify a reason why the feature region in the region of interest does not satisfy the information for selecting an inference unit based on clinical information at the first point of time and clinical information at the second point of time.

15. The information processing apparatus according to claim 14, further comprising a display unit configured to display the identified reason.

16. The information processing apparatus according to claim 1, wherein if a feature region in the region of interest does not satisfy information for selecting an inference unit, at least either a medical image captured at or before the first point of time or a medical image captured at or after the second point of time is substituted as a target of the temporal subtraction image.

17. An information processing method comprising:
    obtaining a temporal subtraction image between a first medical image captured at a first point of time and a second medical image captured at a second point of time; and
    selecting, based on a region of interest in the obtained temporal subtraction image, at least one inference unit from a plurality of inference units, each inference unit for making an inference from the temporal subtraction image,
    wherein in response to being selected by the selecting, the at least one inference unit selected by the selecting makes the inference from the temporal subtraction image.

18. A non-transitory computer-readable storage medium storing a program for causing a computer to execute a process comprising:
    obtaining a temporal subtraction image between a first medical image captured at a first point of time and a second medical image captured at a second point of time; and
    selecting, based on a region of interest in the obtained temporal subtraction image, at least one inference unit from a plurality of inference units, each inference unit for making an inference from the temporal subtraction image,
    wherein in response to being selected by the selecting, the at least one inference unit selected by the selecting makes the inference from the temporal subtraction image.

* * * * *